US006436664B1

(12) United States Patent
Iomantas et al.

(10) Patent No.: US 6,436,664 B1
(45) Date of Patent: Aug. 20, 2002

(54) METHOD FOR PRODUCING SHIKIMIC ACID

(75) Inventors: Yurgis Antanas Vladovich Iomantas; Elena Georgievna Abalakina; Boris Mironovich Polanuer; Tatyana Abramovna Yampolskaya; Tatyana Aleksandrovna Bachina; Yuri Ivanovich Kozlov, all of Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/532,800

(22) Filed: Mar. 21, 2000

(30) Foreign Application Priority Data

Mar. 25, 1999 (RU) .......................................... 990105931
Nov. 3, 1999 (RU) ........................................... 99122932

(51) Int. Cl.[7] .................................................. C12P 1/00
(52) U.S. Cl. ..................... 435/41; 435/64.1; 435/252.5; 435/248; 435/170
(58) Field of Search ....................... 435/69.1, 41, 252.5, 435/248, 170, 93

(56) References Cited

PUBLICATIONS

Shohachiro Yuki, Japan J. Genetics, vol. 50, No. 2, pp. 155–157, "The Chromosomal Location of the Structure Gene for Amylase in Bacillus Subtilis", 1975.

M.M. Campbell, et al., pp. 179–193, The Biosynthesis and Synthesis Of Shikimic Acid, Chorismic Acid, and Related Compounds, Feb. 1993.

Knaggs, 1999. Tne Biosynthesis of Shikimate Metabolites—Review covering 1997. Nat. Prod. Rep., 16:525–560.*

Voet, et al., 1990. Biochemistry, Wiley & Sons, Inc., Canada. pp. 844–845.*

Simonart, et al., Apr. 2, 1960. Nature, 186:78–79.*

DATABASE CA [Online] CHEMICAL ABSTRACTS SERVICE, COLUMBUS, OHIO, US; NAKANE, AKITAKA ET AL: "Nucleotide sequence of the shikimate kinase gene (arol) of Bacillus subtilis" retrieved from STN Datbase accession No. 121:28189 XP002180982 *abstract* & J. FERMENT. BIOENG. (1994), 77(3), 314–14.

DATABASE CA [Online] CHEMICAL ABSTRACTS SERVICE, COLUMBUS, OHIO, US; NASSER, DELILL S. ET AL; "Regulated enzymes of aromatic amino acid synthesis; control, isozymic nature, and aggregation in Bacillus subtilis and Bacillus licheniformis" retrieved from STN Database accession No. 70:111766 XP002180983 *abstract* & J. BACTERIOL. (1969), 98(1), 44–50.

DATABASE CA [Online] CHEMICAL ABSTRACTS SERVICE, COLUMBUS, OHIO US; HOCH, JAMES A. ET AL: "Gene–enzyme relations of aromatic acid biosynthesis in Bacillus subtilis" retrieved from STN Database accession No. 79:134270 XP002180984 *abstract* & J. BACTERIOL. (1973), 116(1), 59–66.

* cited by examiner

*Primary Examiner*—James Ketter
*Assistant Examiner*—Richard Schnizer
(74) *Attorney, Agent, or Firm*—Oblon, Spivak, McClelland, Maier & Neustadt, P.C.

(57) ABSTRACT

A method for producing shikimic acid, comprising the steps of cultivating a bacterium belonging to the genus Bacillus which is deficient in shikimate kinase activity and has shikimic acid productivity, or a bacterium belonging to the genus Bacillus which is deficient in 5-enolpyruvylshikimate-3-phosphate synthase activity and has shikimic acid productivity, in an medium, producing and accumulating shikimic acid in the medium, and collecting shikimic acid from the medium.

15 Claims, 10 Drawing Sheets

METHOD FOR PRODUCING SHIKIMIC ACID

TECHNICAL FIELD

Figure 1A:
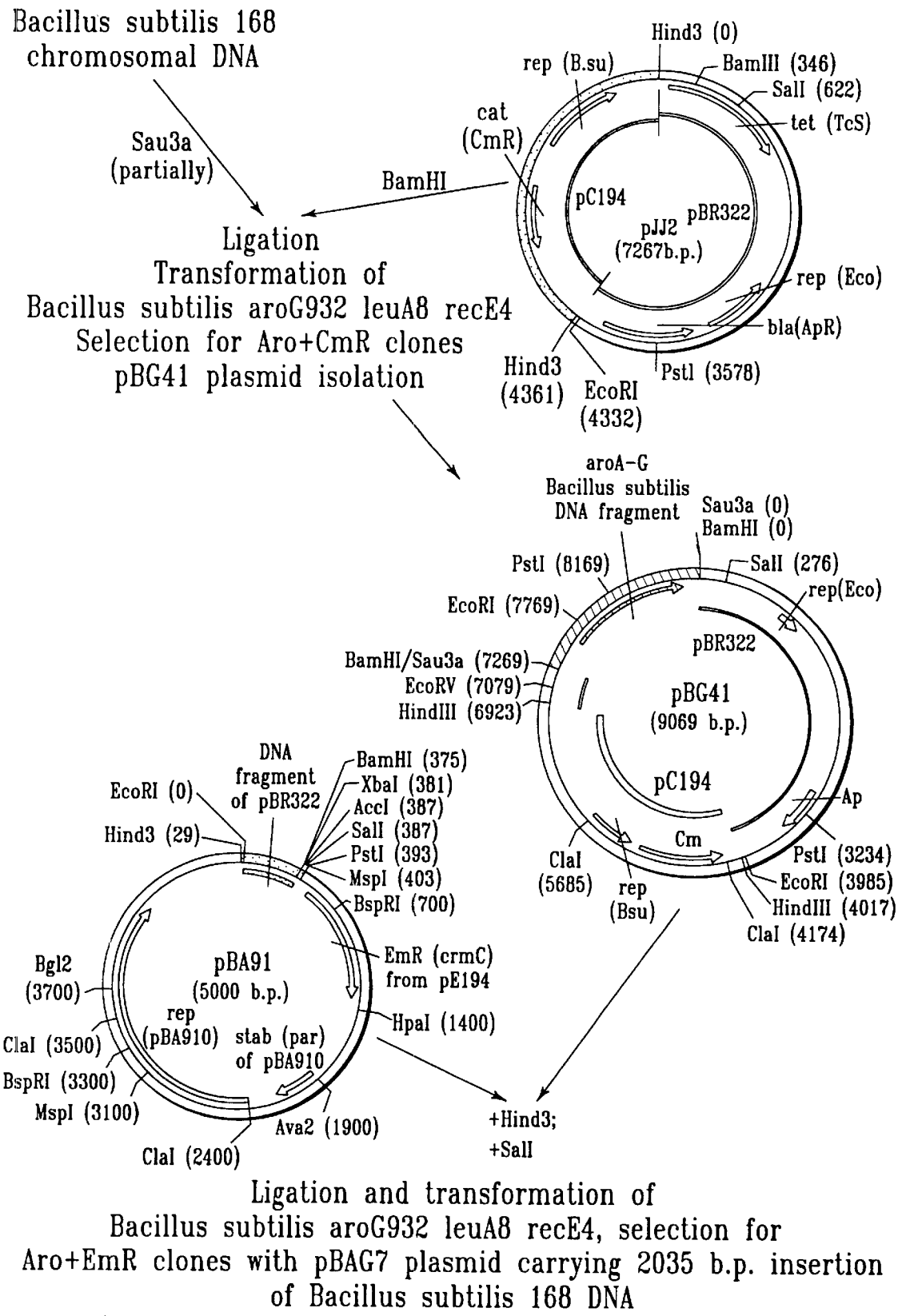

The present invention relates to a method for producing shikimic acid. Shikimic acid is useful for intermediates of aromatic compounds synthesis such as phenylalanine, tyrosine, tryptophane, p-aminobenzoic acid or p-hydroxybenzoic acid. Shikimic acid is also used as component of waste disposal material and the like.

BACKGROUND ART

Shikimic acid that is an aromatic intermediate is synthesized in four enzymatic reactions from phosphoenol pyruvate and erythrose-4-phosphate. These four enzymes are encoded by aroA, aroB, aroC, and aroD genes in *Bacillus subtilis*. Shikimic is converted into chorismic acid by enzymatic reactions by aroI, aroE and aroF. The pathway from phosphoenol pyruvate and erythrose-4-phosphate to chorismic acid is called as shikimic acid pathway. Shikimic acid pathway is also known as a common pathway for biosynthesis of aromatic amino acids L-tryptophane, L-phenylalanine and L-tyrosine.

Shikimic acid is obtained from plants heretofore, and it has not been produced by direct fermentation using microorganism.

*Bacillus subtilis* 1-118 (aroI116, amy4), which has been known as amylase-deficient strain, is known to have a mutation in aroI gene (Yuki, S., Japan. *J. Genetics*, 50(2), 155–157 (1975)). However, it is not known that the strain 1-118 produces shikimic acid.

Although, it also has been known that *Bacillus subtilis* SB130 (aroE130, hisH32) has a mutation in a gene coding for 5-enolpyruvylshikimate-3-phosphate synthase (EC:2.5.1.19), it is not known that the strain produces shikimic acid.

DISCLOSURE OF THE INVENTION

An object of the present invention is to provide a method for producing shikimic acid by direct fermentation and a microorganism that is used in the method.

As a result of diligent and repeated investigation in order to achieve the object described above, the present inventors determined that strains of *B. subtilis*, carrying defective shikimate kinase enzyme accumulated shikimate. Further, the present inventor succeeded in improving shikimic acid productivity of the bacterium by enhancing an activity of shikimate dehydrogenase and an activity of 3-deoxy-D-arabino-heptulosonic acid 7-phosphate synthase (sometimes referred to as "DAHP synthase").

Further, the present inventors found that the shikimic acid productivity of *B. subtilis* strain can be increased by depletion of aroE gene product, 5-enolpyruvylshikimate-3-phosphate, and enhancing the activity of shikimate dehydrogenase synthase, even if the strain possesses active shikimate kinase.

That is, aspects of the present invention are as follows:

(1) A method for producing shikimic acid, comprising the steps of cultivating a bacterium belonging to the genus Bacillus which is deficient in shikimate kinase activity and has shikimic acid productivity in a medium, producing and accumulating shikimic acid in the medium, and collecting shikimic acid from the medium;

(2) The method of (1), wherein the bacterium is *Bacillus subtilis;*

(3) The method of (1), wherein shikimate dehydrogenase activity in the cell of the bacterium is enhanced;

(4) The method of (1), wherein shikimate dehydrogenase activity is enhanced by increasing copy number of a gene encoding shikimate dehydrogenase, enhancing expression regulation sequence of the gene or integrating the gene into chromosomal DNA of the bacterium;

(5) The method of (4), wherein the shikimate dehydrogenase gene, in which its inherent promoter is displaced by a promoter of other gene or to which a promoter of other gene is added, is integrated into the chromosomal DNA;

(6) The method of (5), wherein activity of 3-deoxy-D-arabino-heptulosonic acid 7-phosphate synthase in the cell of the bacterium is further enhanced;

(7) The method of (6), wherein activity of 3-deoxy-D-arabino-heptulosonic acid 7-phosphate synthase is enhanced by increasing copy number of a gene encoding 3-deoxy-D-arabino-heptulosonic acid 7-phosphate synthase, enhancing expression regulation sequence of the gene or integrating the gene into chromosomal DNA of the bacterium;

(8) A bacterium belonging to the genus Bacillus having shikimic acid productivity, wherein the bacterium is deficient in shikimate kinase activity, and shikimate dehydrogenase activity in the cell of the bacterium is enhanced; and (9) The bacterium of (8), wherein activity of 3-deoxy-D-arabino-heptulosonic acid 7-phosphatesynthase in its cell is enhanced.

(10) A method for producing shikimic acid, comprising the steps of cultivating a bacterium belonging to the genus Bacillus which is deficient in 5-enolpyruvylshikimate-3-phosphate synthase activity and has shikimic acid productivity in a medium, producing and accumulating shikimic acid in the medium, and collecting shikimic acid from the medium.

(11) The method of (10), wherein said bacterium is *Bacillus subtilis*.

(12) The method of (10), wherein shikimate dehydrogenase activity in the cell of said bacterium is enhanced.

(13) The method of (12), wherein shikimate dehydrogenase activity is enhanced by increasing copy number of a gene encoding shikimate dehydrogenase, enhancing expression regulation sequence of said gene or integrating said gene into chromosomal DNA of said bacterium.

(14) A bacterium belonging to the genus Bacillus having shikimic acid productivity, wherein said bacterium is deficient in 5-enolpyruvylshikimate-3-phosphate synthase activity, and shikimate dehydrogenase activity in the cell of said bacterium is enhanced.

In the present invention, the term "having shikimic acid productivity" refers to an activity to accumulate shikimic acid in a medium, when the bacterium of the present invention is cultivated in the medium.

The present invention will be explained in detail below.

A bacterium belonging to the genus Bacillus of the first embodiment of the present invention is deficient in shikimate kinase activity. As the bacterium belonging to the genus Bacillus, there are exemplified *Bacillus amyloliquefaciens, Bacillus subtilis* and Bacillus.

A bacterium belonging to the genus Bacillus deficient in shikimate kinase activity is exemplified by a mutant which substantially completely loses shikimate kinase activity and a mutant of which shikimate kinase activity is significantly lower than that of wild type strain. Alternatively, a bacterium belonging to the genus Bacillus may be a strain in which a shikimate kinase gene (aroI) on its chromosome is disrupted by homologous recombination.

Depletion of shikimate kinase activity of the bacterium belonging to the genus Bacillus may be achieved by the conventionally known mutation treatment and selection of mutant strain which has a mutation in its gene coding for the enzyme (aroI). The mutation treatment includes a method for treating the bacterium belonging to the genus Bacillus with ultraviolet irradiation or a mutating agent such as N-methyl-N'-nitro-N-nitrosoguanidine (NTG) and nitrous acid usually used for the mutation treatment.

An aroI mutant of the bacterium belonging to the genus Bacillus may be also obtained by gene conversion method using aroI mutant of a bacterium belonging to the genus Bacillus. That is, a wild type aroI gene on a plasmid is converted to a mutant aroI gene by gene conversion method using the plasmid carrying a cloned aroI gene and a mutant strain having a mutation in its aroI gene. Then a wild type aroI gene in a bacterium belonging to the genus Bacillus is converted to the mutant aroI gene.

Concretely, a bacterium belonging to the genus Bacillus is exemplified by *Bacillus subtilis* 1-118 (aroI116, amy4) and I-116 which was derived from the strain 1-118 (see aftermentioned Example 1) or the like. The strain 1-118 is described in Yuki, S., Japan *J. Genetics*, 50 (2), 155–157 (1975).

A bacterium belonging to the genus Bacillus of the present invention may be preferably enhanced in shikimate dehydrogenase activity. Furthermore, it is preferable that the bacterium is further enhanced in DAHP synthase. Shikimate dehydrogenase activity or DAHP synthase activity in a bacterial cell can be enhanced by, for example, increasing the copy number of genes coding for these enzymes or integrating the genes into chromosomal DNA of the bacterium.

Concretely, enhancement of shikimate dehydrogenase activity may be achieved by constructing recombinant DNA by ligating a gene fragment that codes for shikimate dehydrogenase with a vector that functions in bacteria belonging to the genus Bacillus, transforming a host strain of bacterium belonging to the genus Bacillus by introducing the recombinant DNA to the strain. The shikimate dehydrogenase is coded by aroD gene.

As to the aroD gene, the gene of bacterium belonging to the genus Bacillus and also the gene derived from other organisms can be used.

As for plasmids which are used for introducing aroD gene into cells of bacteria belonging to the genus Bacillus, any plasmid that is replicable in cells of the bacteria, which is concretely exemplified by pUB110, pC194, pE194, pSM19035, pMX30, pMX39, pCB20, pCB30 and pCA1 and the like. Alternatively, the bacteria belonging to the genus Bacillus may be transformed by integrating a linearized DNA into chromosomal DNA instead of using a vector.

In order to prepare recombinant DNA by ligating the aroD gene and a vector that can function in a cell of bacterium belonging to the genus Bacillus, the vector is digested by restriction enzyme(s) corresponding to the termini of a DNA fragment comprising the aroD gene. Ligation is generally performed by using a ligase such as T4 DNA ligase.

To introduce the recombinant DNA prepared as described above to bacterium belonging to the genus Bacillus, any known transformation methods can be employed. For instance, employable are a method of preparing competent cells from cells which are at the growth phase followed by introducing the DNA thereunto [see Duncan, C. H., Wilson, G. A. and Young, F. E., *Gene*, 1, 153 (1977)]. In addition to this, also employable is a method of making DNA-recipient cells into the protoplast which can easily take up recombinant DNAs followed by introducing the recombinant DNA into the cells [see Chang, S. and Choen, S. N., *Molec. Gen. Genet.*, 168, 111 (1979)]. Integrating the aroD gene into chromosomal DNA of a bacterium belonging to the genus Bacillus may be achieved by a congression method employing linearized DNA in which two sequences are randomly integrated into chromosomal DNA (Erickson, R. T. et al., *Genetics*, 73(1), 13 (1973); Nester, E. W. et al., *Genetics*, 48, 529 (1963)).

Other than the above-described gene amplification, enhancement of shikimate dehydrogenase activity can also be achieved by substituting the expression regulation sequence such as promoter of the aroD gene with a more potent one. The expression of aroD gene can be enhanced by introducing a recombinant gene in which aroD structural gene is ligated with a strong promoter into cells of bacteria belonging to the genus Bacillus. Substitution of the expression regulation sequence of aroD gene on the chromosomal DNA may be achieved by the method described in Japanese Patent Laid-Open Publication No. 1-215280. As potent promoters, for example, $Pr_{(rpmA)}$ which is the promoter of the ribosomal protein gene (rpmA) of *Bacillus amyloliquefaciens* is known. By substituting the promoter inherent in aroD gene with these promoters, the expression of aroD gene is enhanced, thereby enhancing shikimate dehydrogenase activity. The enhancement of the expression regulation sequence may be combined by increasing the copy number of aroD gene.

DAHP synthase activity can be enhanced according to the above-described methods in which a gene encoding DAHP synthase (aroA gene) is used in place of aroD gene.

A bacterium belonging to the genus Bacillus of the second embodiment of the present invention is deficient in 5-enolpyruvylshikimate-3-phosphate synthase activity. As the bacterium belonging to the genus Bacillus, there are exemplified *Bacillus amyloliquefaciens*, *Bacillus subtilis* and Bacillus.

A bacterium belonging to the genus Bacillus deficient in 5-enolpyruvylshikimate-3-phosphate synthase activity is exemplified by a mutant which substantially completely loses 5-enolpyruvylshikimate-3-phosphate synthase activity and a mutant of which 5-enolpyruvylshikimate-3-phosphate synthase activity is significantly lower than that of wild type strain. Alternatively, a bacterium belonging to the genus Bacillus may be a strain in which a gene coding for 5-enolpyruvylshikimate-3-phosphate synthase (aroE) on its chromosome is disrupted by homologous recombination.

Depletion of 5-enolpyruvylshikimate-3-phosphate synthase activity of the bacterium belonging to the genus Bacillus may be achieved by the conventionally known mutation treatment and selection of mutant strain which has a mutation in its gene coding for the enzyme (aroE). The mutation treatment includes a method for treating the bacterium belonging to the genus Bacillus with ultraviolet irradiation or a mutating agent such as N-methyl-N'-nitro-N-nitrosoguanidine (NTG) and nitrous acid usually used for the mutation treatment.

An aroE mutant of the bacterium belonging to the genus Bacillus may be also obtained by gene conversion method using aroE mutant of a bacterium belonging to the genus Bacillus. That is, a wild type aroE gene on a plasmid is converted to a mutant aroE gene by gene conversion method using the plasmid carrying a cloned aroE gene and a mutant strain having a mutation in its aroE gene. Then a wild type aroE gene in a bacterium belonging to the genus Bacillus is converted to the mutant aroE gene.

In the present invention, the bacterium belonging to the genus Bacillus which is deficient in 5-enolpyruvylshikimate-3-phosphate synthase is preferably enhanced in shikimate dehydrogenase activity. Furthermore, it is preferable that the bacterium is further enhanced in DAHP synthase. Shikimate dehydrogenase activity or DAHP synthase activity in the bacterial cell can be enhanced in the same manner as the bacterium used in the first embodiment of the present invention.

In a bacterial cell shikimic acid is converted to shikimate 3-phosphate by action of shikimate kinase enzyme. Shikimic acid was found to be a product inhibitor of shikimate dehydrogenase in *B. subtilis*, like as in *E. coli* cells. On the other side, shikimate 3-phosphate do not inhibit shikimate dehydrogenase. The inventors supposed that the feedback inhibition of shikimate dehydrogenase by shikimic acid may be desensitized by increasing shikimate kinase activity, since shikimate kinase reduces an intracellular concentration of shikimate.

Then the inventors tested possibility to construct a shikimate producer carrying a gene encoding an active shikimate kinase. As a result it was found that *Bacillus subtilis* having the active shikimate kinase gene exhibits an activity to produce shikimic acid by deleting 5-enolpyruvylshikimate-3-phosphate synthase, and the productivity is increased by further enhancing the shikimate dehydrogenase activity. That is, the accumulating shikimate 5-phosphate formed by shikimate kinase are easily dephosphorylated by action of phosphatases and the resulting shikimic acid is exported from bacteria.

Shikimic acid can be produced by cultivating in a medium a bacterium belonging to the genus Bacillus having shikimic acid productivity, which is obtainable as described above, producing and accumulating shikimic acid in the medium, and collecting shikimic acid from the medium.

The medium to be used for cultivation is an ordinary medium containing a carbon source, a nitrogen source, organic ions and optionally other organic components.

As the carbon source, it is possible to use sugars such as glucose, galactose, fructose, or starch hydrolysate; alcohols such as glycerol or sorbitol; or organic acids such as fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as vitamin B1 and L-isoleucine or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16–72 hours. The cultivation temperature is controlled at 25C. to 45C., and pH is controlled at 5–8 during cultivation. Inorganic or organic, acidic or alkaline substances as well as ammonia gas or the like can be used for pH adjustment.

Collection of shikimic acid from a fermented liquor is usually carried out by combining an ion exchange resin method, a precipitation method and the like.

BRIEF DESCRIPTION OF DRAWINGS

FIG. 1 shows construction of the plasmid pBAG7 which contains aroA gene derived from *B. subtilis* 168, FIG. 2 shows bifunctional plasmid pMX39, which is able to replicate in *B. subtilis* and *E. coli,*

FIG. 3 shows a structure of the plasmid pAD2 which contains aroD gene,

FIG. 4 shows steps of minimizing the plasmid pAD2 which contains aroD gene,

FIG. 5 shows a structure of the plasmid pCA1,

FIG. 6 shows a structure of the plasmid pDP4 which contains aroD gene,

FIG. 7 shows steps of integrating $Pr_{(rpmA)}$-pheA DNA fragment into chromosome of *B. subtilis* SB112, trpC2, pheA112 to obtain a strain A10, FIG. 8 shows steps of integrating aroA gene into chromosome of *B. subtilis* A10 to obtain a *B. subtilis* strain d3, FIG. 9 shows a structure of chromosome fragment of *B. subtilis* ID3 in which aroD gene is integrated, and FIG. 10 shows a structure of plasmid pAAP6 which contains aroA gene.

FIG. 11 shows a procedure of integrating aroA gene into chromosome of *B. subtilis* strin ID3.

BEST MODE FOR CARRYING OUT THE INVENTION

<1> Analysis of Shikimic Acid and Dehydroshikimic Acid in Fermentation Broth

In the following examples, shikimic acid and dehydroshikimic acid were analyzed as follows.

1. Sample Preparation

The samples of fermentation broth were centrifuged 5 min on model 5415C microfuge (Eppendorf, Germany) with the aim to remove cells and debris. Supernatant was diluted 30 times with water and used for HPLC analysis without further purification.

2. Reversed-phase Separation

The analysis was carried out using isocratic system which consists of model 510 pump, model 990 diode-array detector with IBM-PC based data station (both Waters, Milford, USA) and model 7010 injector with 1 μl internal sample loop (Rheodyne, Cotati, USA). All the separations was carried out on reversed phase (C18) column 150×3.3 mm ID packed with 5 μm Separon C18 sorbent (Tessek, Cheh republic) at the room temperature.

Eluent containing 0.5% acetic acid and 0.7%triethylamine (pH 6) was degassed on ultrasonic bath. Typically eluent flow rate was equal to 0.3 ml/min. In the above condition shikimic acid is eluted faster than dehydroshikimic acid. An analysis was completed in about 7 minutes.

3. Aminophase Separation

All analysis carried out using the same isocratic HPLC system containing model 510 pump and model 990diode-array detector equipped with 990 software (both Waters, USA) and model 7010 injector with 1 μl sample loop (Rheodyne, USA).

150×3.3 mm ID glass column packed with 5 μm $NH_2$sorbent (Tessek, Cheh Republic) with laboratory made water-circulation jacket was used. Analysis was carried out under following conditions.

column temperature: equal to 50° C., eluent: containing 60% of acetonitrile and 6 g/l of ammonium acetate, flow rate: 0.5 ml/min.

In the above condition shikimic acid is eluted faster than dehydroshikimic acid. An analysis was completed in about 7 minutes.

<2> Cultivation by Jar Fermenter In the following examples, B. subtilis strains were cultivated as follows.

1. Seed Culture

The strain was grown on plates or slants with LB-medium medium agar containing 10 mg/l of erythromycin (Em) at 37° C. for 24 hours. And then the strain was inoculated into 30 ml LB-medium used as the seed medium in flasks with capacity of 700 ml. The seed culture was incubated on a rotary shaker at 37° C. for 6–7 hours.

2. Fermentation in Jar Fermenter

The cultivation of shikimate producer was carried out in "Marubishi" laboratory fermenter (v=1–1.2 L). Any aromatic amino acid (phenylalanine, tryptophane and tyrosine) was not added in the following medium because yeast extract contains them.

The composition of initial fermentation medium (in g/l):

Glucose: 100
(plus up to 150 grams per liter added with feeding solution)
$NH_4Cl$: 3
$(NH_4)_2SO_4$: 2
$KH_2PO_4$: 3
$MgSO_4$: 0.4
$FeSO_4$: 0.02
Yeast extract: 15
("Sigma", Y4OOO)
Erythromycin: 10 mg/l
pH: 7.0

Initial volume of medium in fermenter: 500 ml
Inoculum size: 6% (6 hour culture in 30 ml of LB-medium+10 mg/l of Em).
The feeding solution (up to 200–250 ml): 700 g/L glucose.
Feeding rate:
from the beginning of fermentation up to 19hours: 3–3.2 ml/l.h
after 19 hours: 4.5 ml/l.h
Temperature: 37° C.;
Agitation: 1000–1100 rpm;
Air: 0.6 l/min.

EXAMPLE 1

Figure 2:
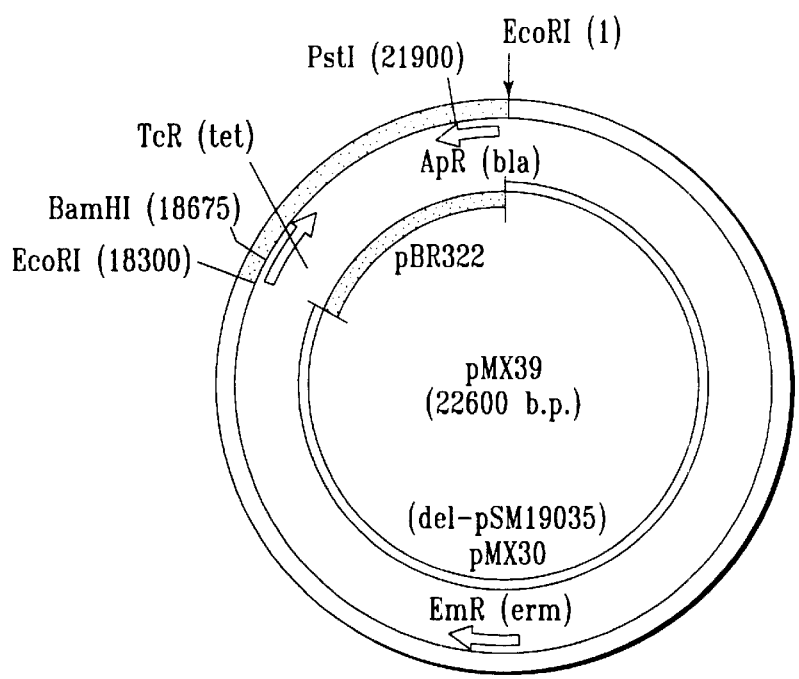

Construction of Bacillus subtilis Carrying aroD Gene Encoding Shikimate Dehydrogenase of Bacillus amyloliquefaciens <1> Cloning of aroD Gene From Bacillus amyloliquefaciens The gene encoding shikimate dehydrogenase (aroD) was cloned from Bacillus amyloliquefaciens strain on plasmid vector. For the cloning a plasmid pMX39 was used, which carries erm gene of resistance to erythromycin. The pMX39 (22.4 kbp) is bifunctional plasmid able to replicate in B. subtilis and E. coli strains (FIG. 2). The Plasmid consists of two genomes, pBR322 (bla, tet) and pMX30 (erm). They were connected at EcoRI restriction site. The pMX30 plasmid (18 kbp) is deletion derivative of pSM19035 (erm) plasmid isolated from Streptococcus pyogenes strain (Rabinovich, P. M. et al., "Cloning of genetic material in Bacilli" In: "Genetics and biotechnology of Bacilli" A. I. Ganesan and J. A. Hoch eds., Academic Press, USA (1984) p.297–308). The plasmids pSM19035, pMX30 and pMX39 replicates in Bacillus strains and has a copy number of about 2–3 per chromosome. The small deletion derivatives, pCB20, pCB30 and pCA1 have increased the copy number up to 30–50 per chromosome.

Figure 3:
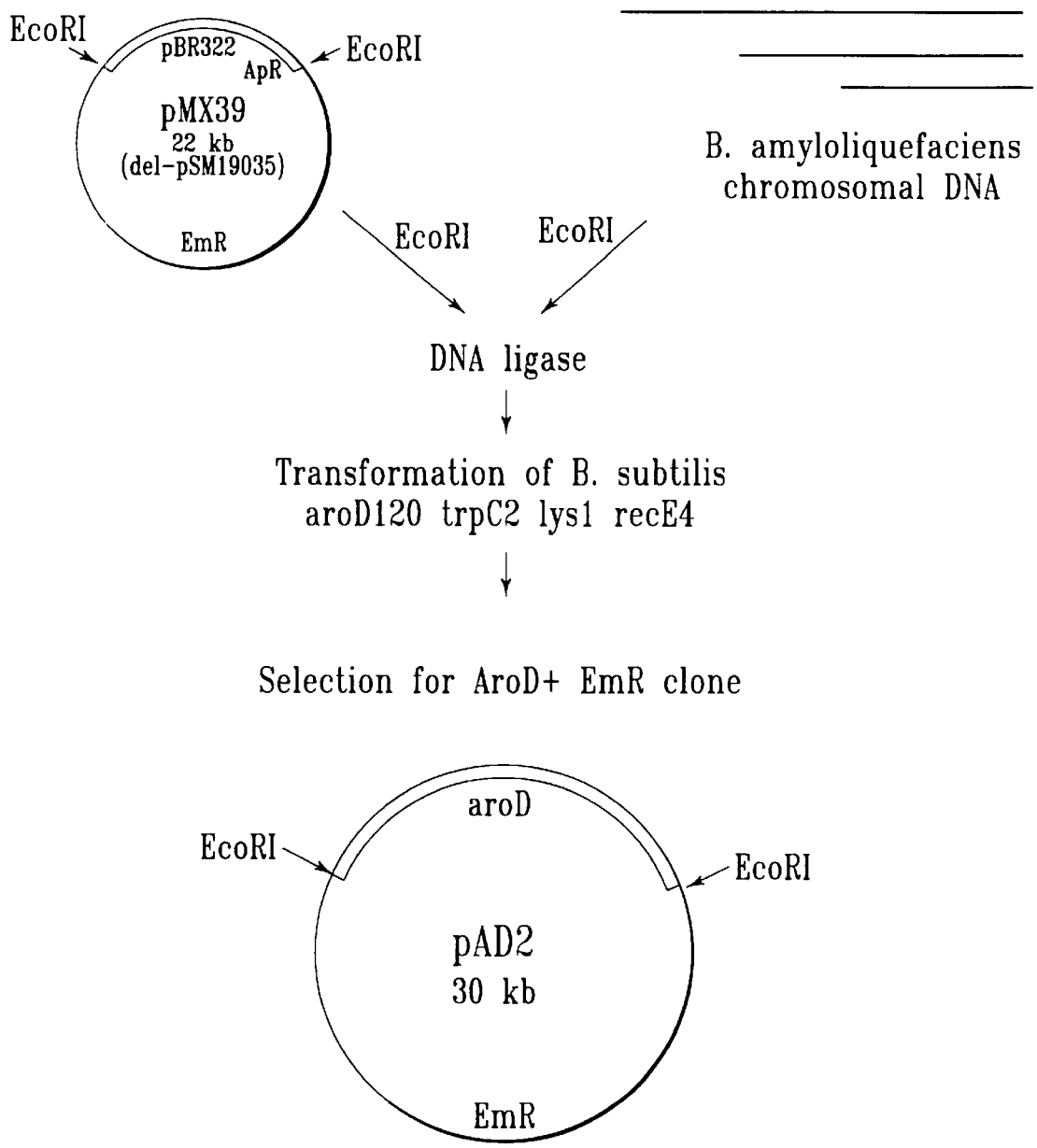
Figure 4:
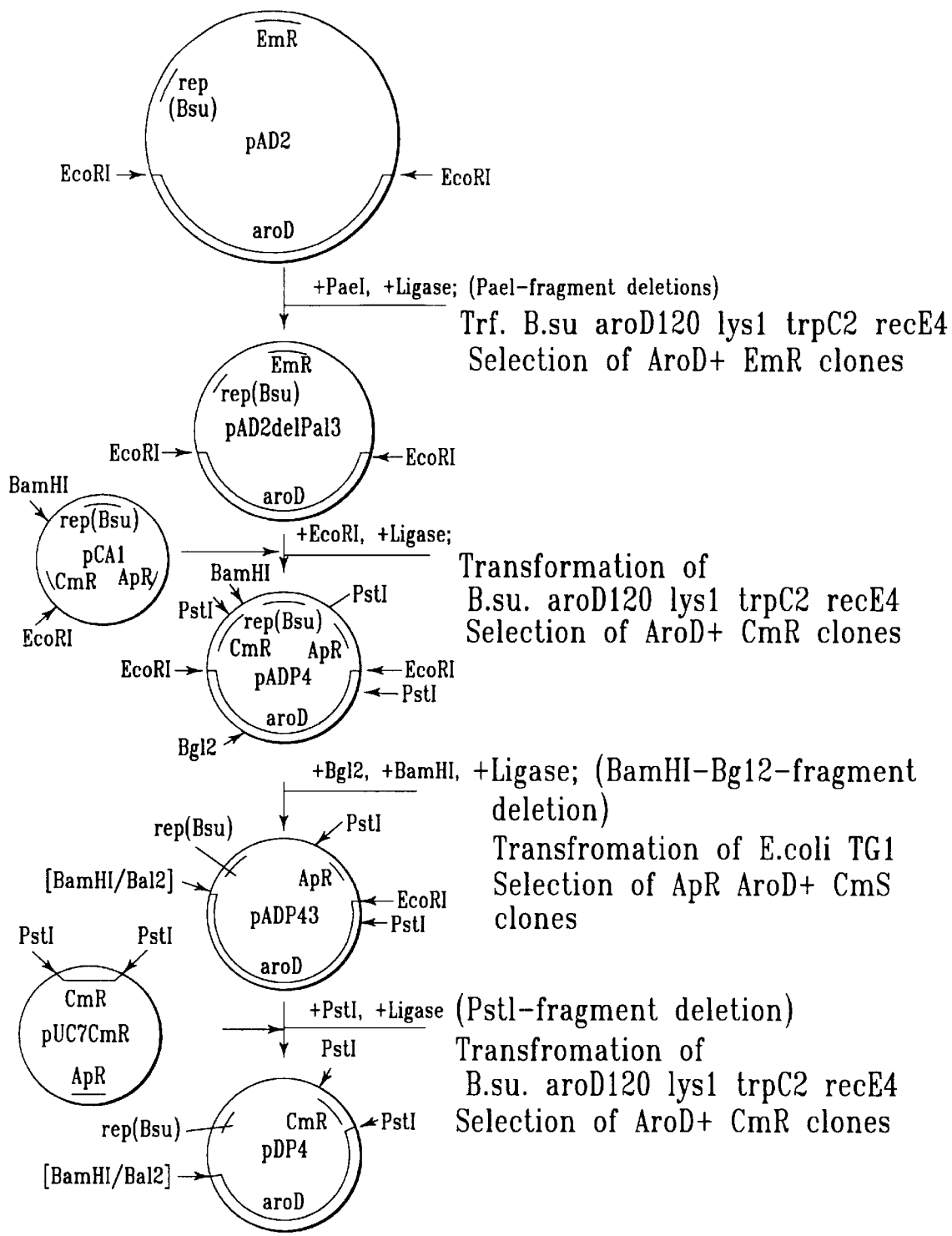

To clone the aroD gene the B. amyloliquefaciens chromosomal DNA was cut by EcoRI restriction enzyme and ligated with pMX39 plasmid DNA EcoRI-fragments (FIG. 3). The DNA was transformed into B. subtilis aroD120, lys1, trpC2, recE4 recipient strain (deposited in Russian National Collection of Industrial Microorganisms (VKPM) Depositary, GNIIgenetika; 1, Dorozhny Proezd., 1, 113545, Moscow, Russia, under a Registration number of VKPM B-1403, and also deposited in Bacillus Genetic Stock Center, The Ohio State University, Department of Biochemistry, 484 West Twelfth Avenue, Columbus, Ohio 43210 USA, under a Registration number of BGSC 1A8) and $Em^R$, $AroD^+$ clones were selected. The isolated recombinant plasmid was named as pAD2 (FIG. 4). The pAD2 (erm, $aroD^+$) plasmid was 30 kbp size and carried B. amyloliquefaciens 12 kbp DNA insertion, containing aroD gene of B. amyloliquefaciens.

The long DNA fragment which carries aroD gene was minimized by cutting it by different restriction enzymes and subcloned into small multicopy vectors. The first step has been performed by cutting pAD2 DNA with PaeI (SphI) restriction enzyme. The cloned B. amyloliquefaciens DNA fragment on pAD2 plasmid has more than eight PaeI restriction sites, but the vector part of plasmid did not have PaeI sites. Thus, the restriction with PaeI and self-ligation of plasmid pAD2 allowed reducing a size of cloned DNA fragment. To do it the mixture of ligated PaeI DNA fragments was transformed into B. subtilis aroD120, lys1, trpC2, recE4 recipient strain. The $AroD^+$, $Em^R$ clones were selected and plasmids DNA were isolated. The resulted plasmid pAD2delPae3(erm, $aroD^+$) carried the 7 kbp DNA fragment with aroD gene.

Figure 5:
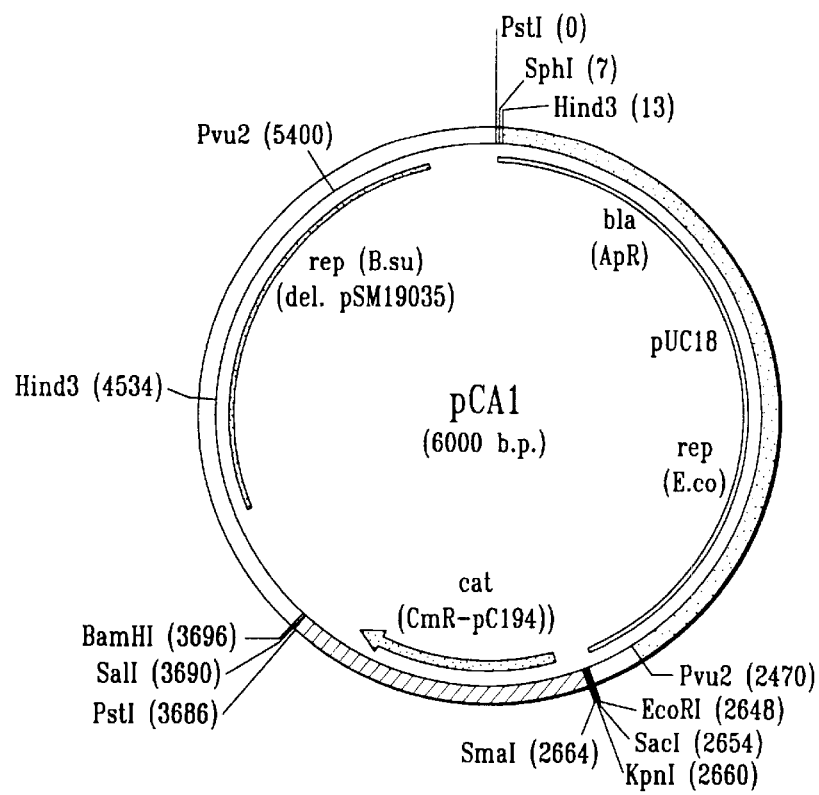

The 7 kbp EcoRI DNA fragment was subcloned from the pAD2Pae3 plasmid into multicopy (30) pCA1 plasmid vector (FIG. 5), carrying cat gene for resistance to chloramphenicol. The resulted plasmid was designated as pADP4 (cat, $aroD^+$). The DNA fragment on pADP4 had a single BglII restriction site, which divided the cloned DNA fragment of B. amyloliquefaciens in half.

Bacillus subtilis aroD120, lys1, trpC2, recE4 which harbors the plasmid pADP4 has been deposited in Russian National Collection of Industrial Microorganisms (VKPM) Depositary, GNIIgenetika; 1, Dorozhny Proezd, 1,113545, Moscow, Russia, under a Registration number of VKPM B-7692 from Dec. 3, 1998.

The 4 kbp BglII-PstI DNA fragment on pADP4 plasmid carried aroD gene of B. amyloliquefaciens. This fragment was used as to construct new plasmids and was used to integrate the aroD gene into B. subtilis chromosome (mentioned later).

In purpose to cut of a part not carrying aroD gene from pADP4 plasmid, the DNA was linearized by BglII and BamHI restriction enzymes, ligated by DNA ligase and transformed into E. coli TG1 strain. The clones resistant to ampicillin were selected. The resulted pADP43 ($aroD^+$) plasmid was able to replicate and complement aroD120 mutation of B. subtilis strain. The plasmid has not drug resistance marker, but it has the pSM19035 plasmid replicon for amplification in Bacillus strains.

Figure 6:
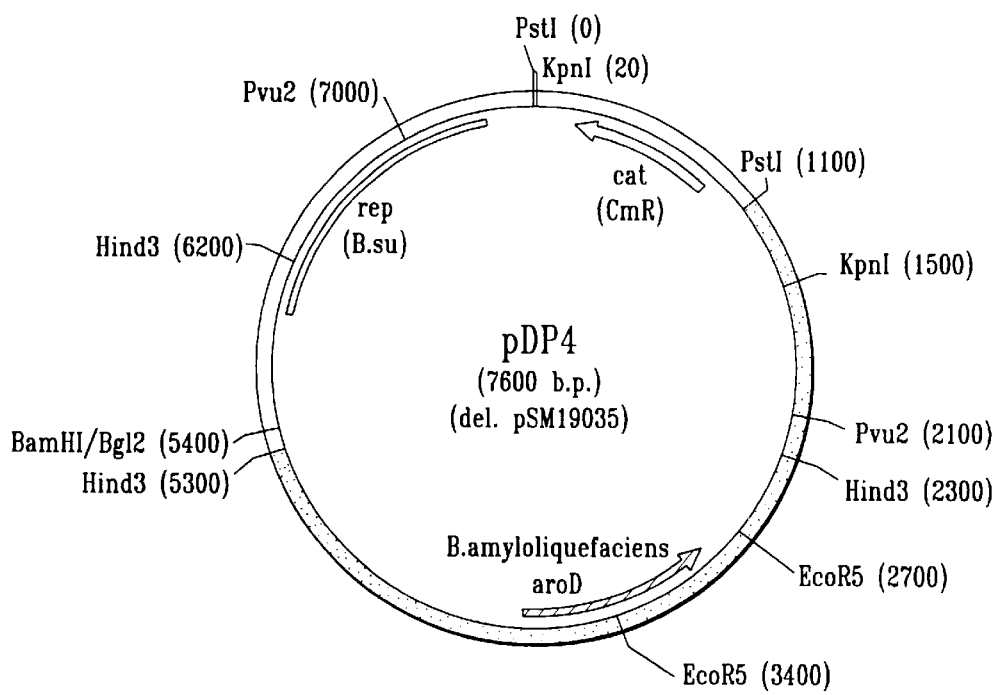

At the next step, DNA template of pUC18 plasmid which is derived from pCA1 was eliminated from pADP43 and the plasmid was marked with the cat gene of resistance to chloramphenicol. To perform this, pUC7 ($Cm^R$) plasmid (purchased from BRL) was used, which contains the cat gene of Staphylococcus aureus flanked by symmetrical polylinker. The pADP43 and pUC7 plasmid DNAs were cut by PstI and ligated. The ligation mixture was transformed into *B. subtilis* aroD120, lys1, trpC2, recE4 strain. The AroD$^{++}$, Cm$^R$ transformants were selected and the new recombinant plasmid pDP4 (cat, aroD$^+$) was isolated. The DNA fragment of *B. amyloliquefaciens* in pAD2 was minimized to 3.5 kb (FIG. 6).

Figure 1B:
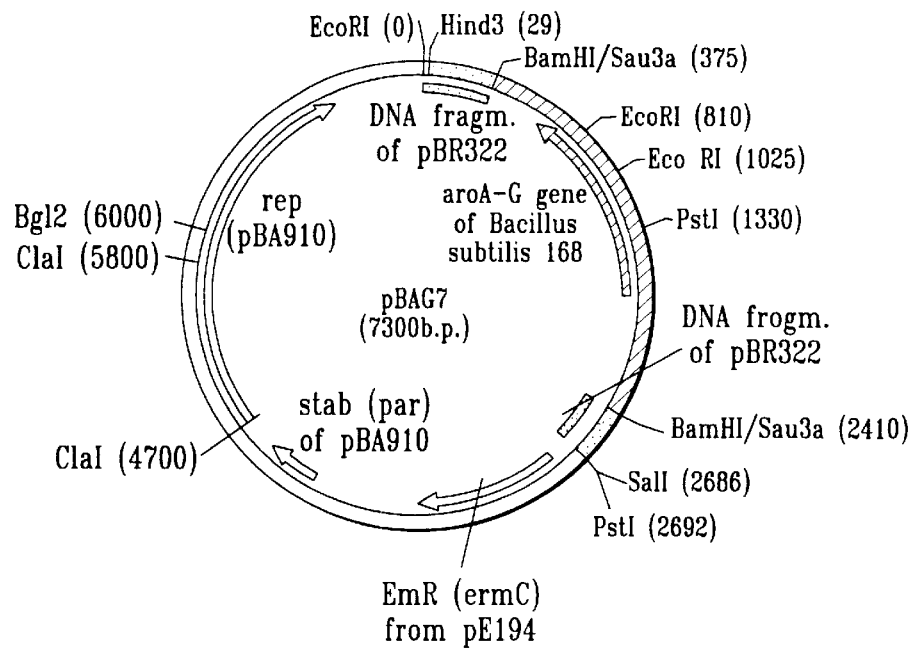

<2> Production of Shikimate and Precursor Dehydroshikimate by *B. subtilis* Strains Harboring aroD Gene A recE$^-$ strain was derived from *B. subtilis* strain 1-118 (aroI116, amy4) and the resulting strain was designated as aroI116. The strain aroI116 was transformed with pDP4 and pBAG7 which contains aroA gene derived from *B. subtilis* 168 to obtain aroI116 (pDP4) and aroI116 (pBAG7), respectively. The construction of pBAG7 is shown in FIG. 1. *B. subtilis* aroI116 (pBAG7) has been deposited in Russian National Collection of Industrial Microorganisms (VKPM) Depositary, GNIIgenetika; 1,Dorozhny Proezd, 1, 113545, Moscow, Russia, under a Registration number of VKPM B-7756 from Mar. 1, 1999.

*B. subtilis* strains aroI116, aroI116 (pDP4) and aroI116 (pBAG7) were cultivated and shikimic acid (SH) and dehydroshikimic acid (DHSH) in the fermentation medium were analyzed as described above. The result is shown in Table 1. Further, shikimate dehydrogenase activity in crude extract of *B. subtilis* strains aroD120, lys1, trpC2, recE4, ATCC6051 Marburg (wild type), aroI116, A5 (2468, aroI116), aroD120, lys1, trpC2, recE4(pDP4) and aroI116(pDP4) was measured. The result is shown in Table 2.

TABLE 1

| Strain | Time Hr | OD 540 nm (1 = 1 cm) | Shikimate g/l | Dehydro-Shikimate g/l | Ratio DHSH/SH |
| --- | --- | --- | --- | --- | --- |
| AroI116 | 24 | 68.8 | 3.1 | 4.8 | 1.5 |
|  | 45 | 53.4 | 5.9 | 8.0 | 1.3 |
|  | 70 | 45.2 | 8.5 | 9.5 | 1.1 |
| AroI116 (pDP4) | 24 | 62.0 | 6.5 | 1.9 | 0.29 |
|  | 45 | 43.0 | 14.0 | 3.6 | 0.25 |
|  | 70 | 36.4 | 14.0 | 6.8 | 0.48 |
| AroI116 (pBAG7) | 24 | 77.6 | 4.9 | 14 | 2.8 |
|  | 45 | 76.8 | 8.0 | 24 | 3.0 |
|  | 70 | 65.6 | 7.2 | 20 | 2.7 |

TABLE 2

| Strain (genotype) | Specific activity (nM/min · mg) |
| --- | --- |
| aroD120, lys1, trpC2, recE4 | 0 |
| ATCC6051 Marburg (wild type) | 5.2 |
| aroI116 | 6.6 |
| A5 (2468, aroI116) | 5.4 |
| aroD12O, lys1, trpC2, recE4 (pDP4) | 391.0 |
| aroI116 (pDP4) | 382.2 |

EXAMPLE 2

Construction of aroD Gene Integrants

<1> Integration of aroD Gene of *B. amyloliquefaciens* into the Chromosome of *B. subtilis* aroI116

As described above, *B. subtilis* aroI116 shikimate producer which carries pDP4 plasmid produced shikimate (around 14 g/l), two times less of dehydroshikimate (precursor) and had 50 times higher activity of shikimate dehydrogenase than the strain without plasmid. However, pDP4 plasmid was segregationally unstable. The 90% of cells lost the plasmid after 24 hours of fermentation. Therefore, the aroD gene of *B. amyloliquefaciens* was integrated into the chromosome of *B. subtilis* aroI116 shikimate producer.

Figure 7:
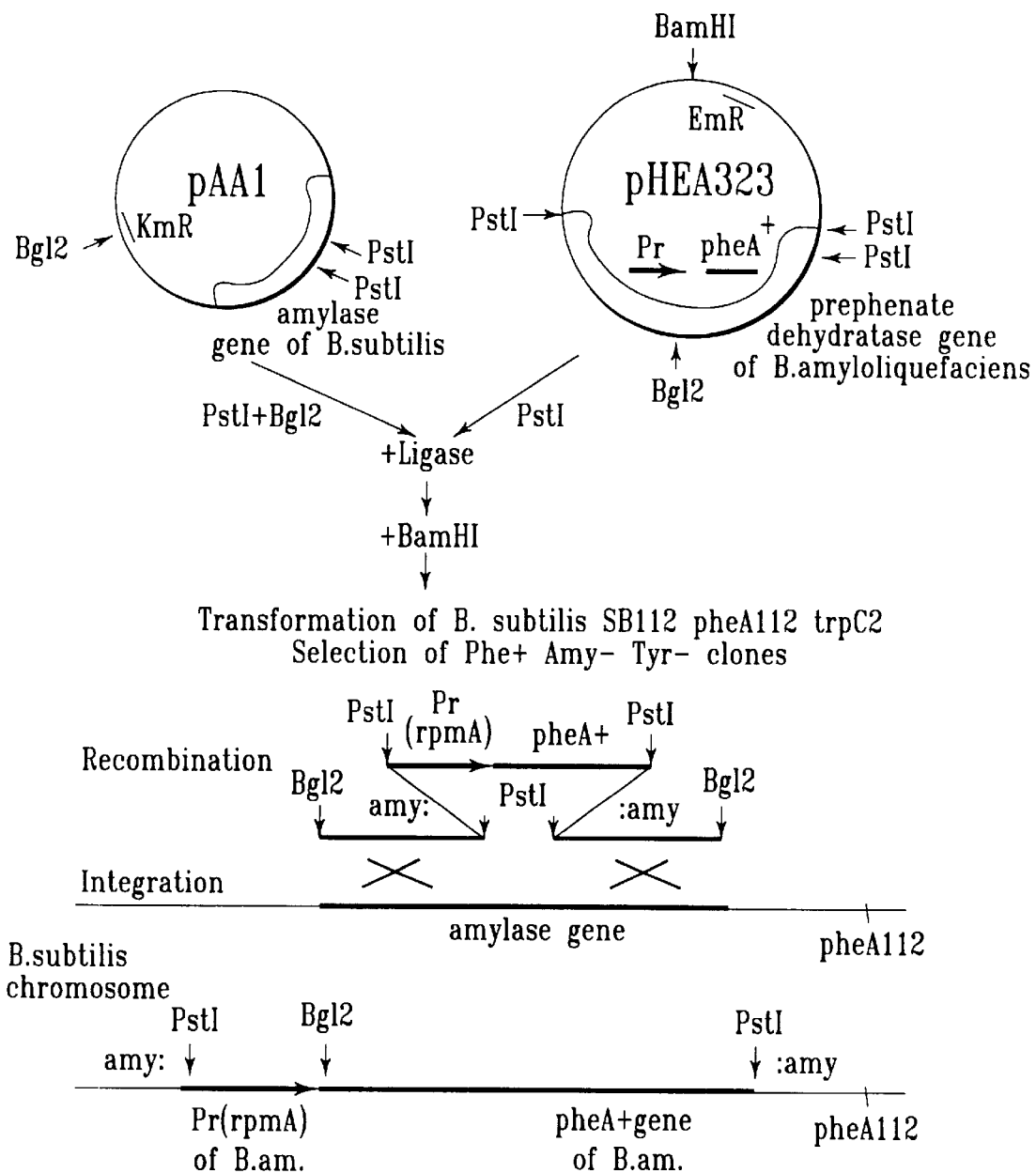

The target type integration method for aroD gene integration in chromosome was developed (FIG. 7). It comprises the following steps:

(1) The alpha amylase gene of *B. subtilis* was cloned on plasmid pAA1 (Cm$^R$, Km$^R$, Amy$^+$). *B. subtilis* 21, amy4, recE4 harboring pAA1 has been deposited in Russian National Collection of Industrial Microorganisms (VKPM) Depositary, GNIIgenetika; 1, Dorozhny Proezd., 1,113545, Moscow, Russia, under a Registration number of VKPM B-7693 from Dec. 3, 1998.

(2) The prephenate dehydratase gene pheA of *B. amyloliquefaciens* was cloned on plasmid pHEA32(PheA$^+$, Em$^R$).

(3) The pHEA32 plasmid was modified. The prephenate dehydratase gene pheA was cloned under strong promoter Pr$_{(rpmA)}$ of ribosomal protein gene rpmA of *B. amyloliquefaciens* on plasmid pHEA323 (P$_{(rpmA)}$-pheA, Em$^R$). *B. subtilis* SB112, trpC2, pheA112 harboring pHEA323 has been deposited in Russian National Collection of Industrial Microorganisms (VKPM) Depositary, GNIIgenetika; 1, Dorozhny Proezd., 1, 113545, Moscow, Russia, under a Registration number of VKPM B-7694from Dec. 3, 1998.

(4) The DNA fragment which carries strong promoter Pr$_{(rpmA)}$ and prephenate dehydratase gene pheA was inserted into alpha amylase gene of *B. subtilis* on plasmid pAA1. The resulting plasmid was linearized and introduced into *B. subtilis* pheA112 strain.

(5) The Pr$_{(rpmA)}$-pheA DNA fragment of *B. amyloliquefaciens* was integrated into amylase gene on the chromosome of *B. subtilis* SB112, trpC2, pheA112 (deposited in Russian National Collection of Industrial Microorganisms (VKPM) Depositary, GNIIgenetika; 1,Dorozhny Proezd., 1, 113545,Moscow, Russia, under a Registration number of VKPM B-1734, and also deposited in Bacillus Genetic Stock Center, The Ohio State University, Department of Biochemistry, 484 West Twelfth Avenue, Columbus, Ohio 43210 USA, under a Registration number of BGSC 1A227) with the help of homologous recombination between amylase genes on plasmid and on chromosome.

The integrants were selected by complementation of pheA mutation. The constructed strain *B. subtilis* A10 (trpc2, pheA112, any::Pr$_{(rpmA)}$-pheA) had insertion in chromosome, consisting of strong promoter and prephenate dehydratase gene of *B. amyloliquefaciens*. The integrated DNA fragment complemented pheA112 mutation of that strain. The strain had Phe$^+$, but Amy$^-$ and Tyr$^-$ phenotype.

The tyrosine auxotrophy was caused by utilization of all prephenic acid in bacteria and shortage of prephenate to tyrosine biosynthesis. It was a result of pheA gene expression under strong Pr$_{(rpmA)}$ promoter and very high activity of prephenate dehydratase enzyme in the bacteria (the enzyme activity increased more than 5000 times).

In further, the Pr$_{(rpmA)}$-pheA insertion was used as a platform for the insertion of aroD gene of *B. amyloliquefaciens*.

(6) The integrated DNA fragment (amy::Pr$_{(rpmA)}$-pheA) was transferred from *B. subtilis* A10 strain into chromosome of *B. subtilis* aroD120, lys1, trpC2 by using a congression method in transformation with high concentration of chromosomal DNA (Erickson, R. T. et al., *Genetics*, 73(1), 13, (1973); Nester, E. W. et al., Genetics, 48, 529 (1963)).

The constructed *B. subtilis* A10 aroD120 strain had amy::Pr$_{(rpmA)}$-pheA, trpC2, aroD120 genotype and Amy$^-$, Tyr$^-$ and Aro$^-$ phenotype.

Figure 8:
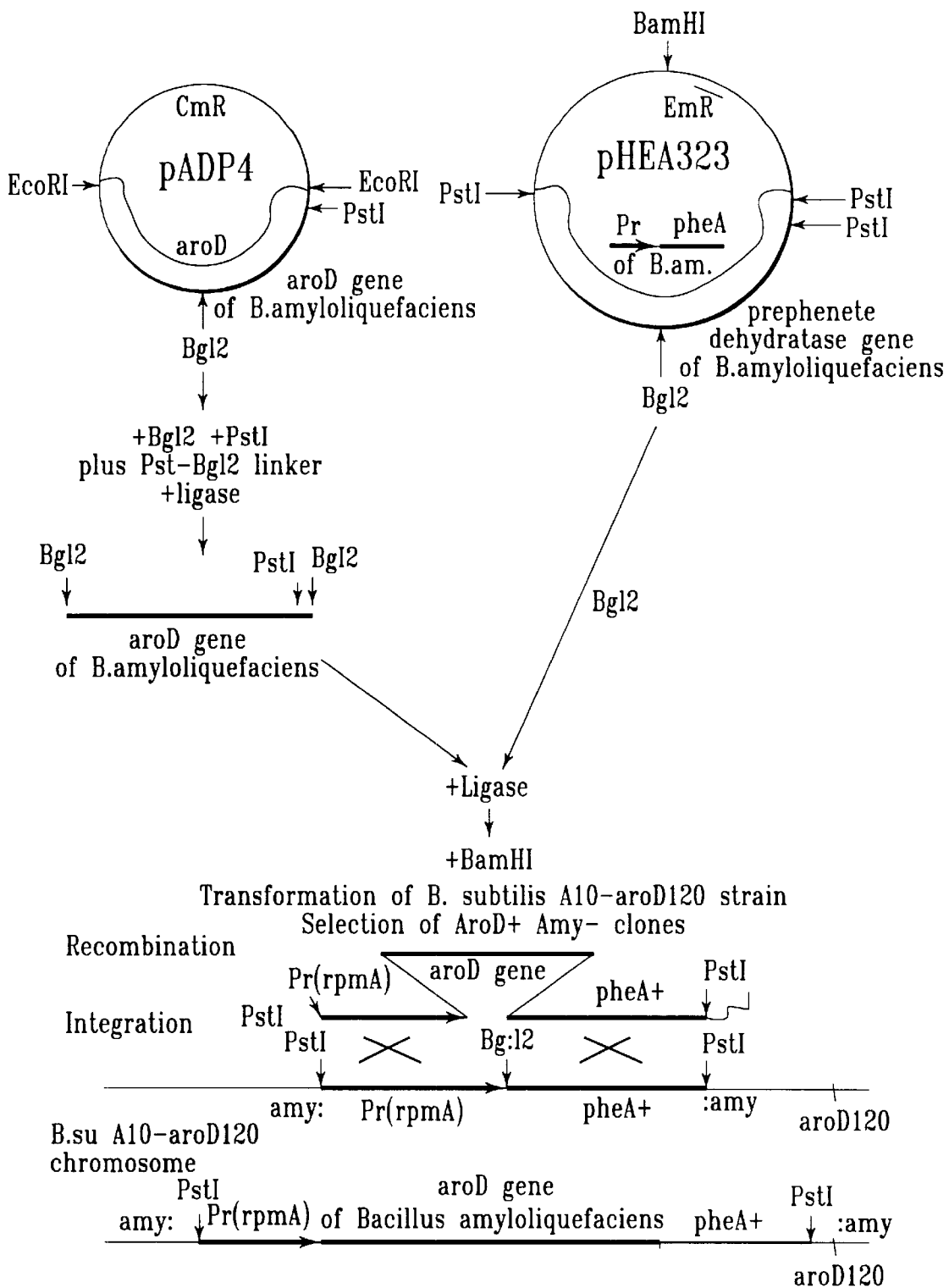

(7) Later, the aroD gene was integrated into chromosome (FIG. 8). The DNA fragment which carries aroD gene of *B. amyloliquefaciens* was inserted between Pr$_{(rpmA)}$ promoter and pheA gene. Such structure $Pr_{(rpmA)}$-aroD$^{(+)}$-pheA was generated in vitro by ligating the DNA of plasmids pHEA323 and pADP4. The resulted DNA ligation mixture was transformed into auxotrophic B. subtilis A10-aroD120 (amy::$Pr_{(rpmA)}$-pheA, trpC2, aroD120) strain. The Aro$^+$, Tyr$^+$ and Amy$^-$ prototrophic clones were selected. After double-cross recombination event the DNA fragment which carries aroD gene was integrated in chromosome between $Pr_{(rpmA)}$ promoter and pheA gene and the $Pr_{(rpmA)}$-aroD$^{(+)}$-pheA structure was formed. The resulted strain B. subtilis d3 had genotype of aroD120, trpC2, amy::$Pr_{(rpmA)}$-aroD$^{(+)}$-pheA. Further, this insertion was transduced into a shikimate producer.

The transfer of promoter $Pr_{(rpmA)}$ and aroD gene integrated in chromosome into shikimate producer.

The integrated genes in B. subtilis d3 strain with antibiotic resistance markers (Em$^R$, Cm$^R$) was marked and all complex were transferred into B. subtilis aroI116 shikimate producer by a transducing phage AR9. To do it the pAE7 plasmid was constructed, which is able to integrate into chromosome of B. subtilis d3 strain. The pAE7 had a cloned fragment of amylase gene, a cat-gene (chloramphenicol acetyltransferase) (Cm$^R$), emr-gene (RNA methylase) (Em$^R$) and pUC19 (Ap$^R$) replicon. The pAE7plasmid (Ap$^R$, Em$^R$, Cm$^R$, amy$^-$) did not replicate in B. subtilis cells, but after transformation it was able to integrated into B. subtilis chromosome in amylase gene by single cross recombination act by Campbell type integration.

Figure 9:
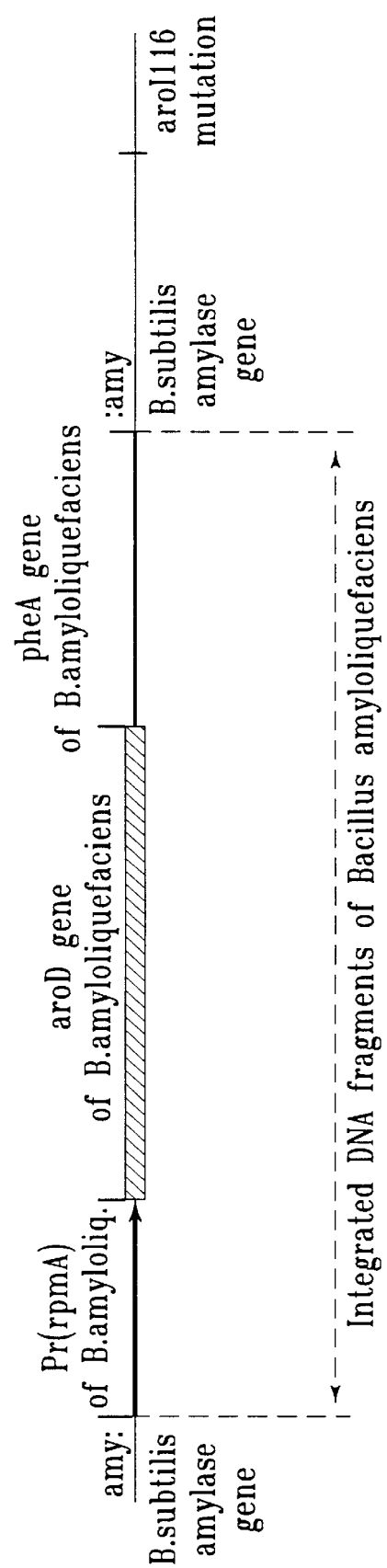

Thus, B. subtilis d3 strain was marked. The resulted strain was named as B. subtilis d3-pAE7(trpC2, aroD120, amy::Pr$_{(rpmA)}$-aroD$^{(+)}$-pheA; amy::pAE7) (Cm$^R$, Em$^R$). It carried two integrations closely located to each other (FIG. 9). A transducing phage AR9 was used to transfer these two integrated structures from B. subtilis d3-pAE7 strain into B. subtilis aroI116 chromosome of shikimate producer. The Em$^R$ and Cm$^R$ markers were used for selection of transductants.

Thus, the new shikimate producing strain B. subtilis d3-pAE7-aroI116 (aroI116, amy4, amy::$Pr_{(rpmA)}$-aroD$^{(+)}$-pheA; amy::pAE7, Cm$^R$, Em$^R$) which carries additional integrated genes was constructed. The integrated pAE7 plasmid was eliminated by growing strain in medium without antibiotics. It resulted the new shikimate producer B. subtilis ID3 (aroI116, amy4, amy::$Pr_{(rpmA)}$-aroD$^{(+)}$-pheA). This shikimate producer contains two copies of aroD gene in chromosome. One is parental gene and the other is integrated gene (FIG. 9). The strain B. subtilis ID3 has 8 times higher activity of shikimate dehydrogenase (Table 5, mentioned later) than B. subtilis aroI116. In laboratory fermenter the B. subtilis ID3 strain produced 11–12 g/l shikimate. B. subtilis ID3 has been deposited in Russian National Collection of Industrial Microorganisms (VKPM) Depositary, GNIIgenetika; 1, Dorozhny Proezd., 1,113545, Moscow, Russia, under a Registration number of VKPM B-7755 from Mar. 1, 1999.

<3> Introduction of aroA Gene into aroD Integrants

Figure 10:
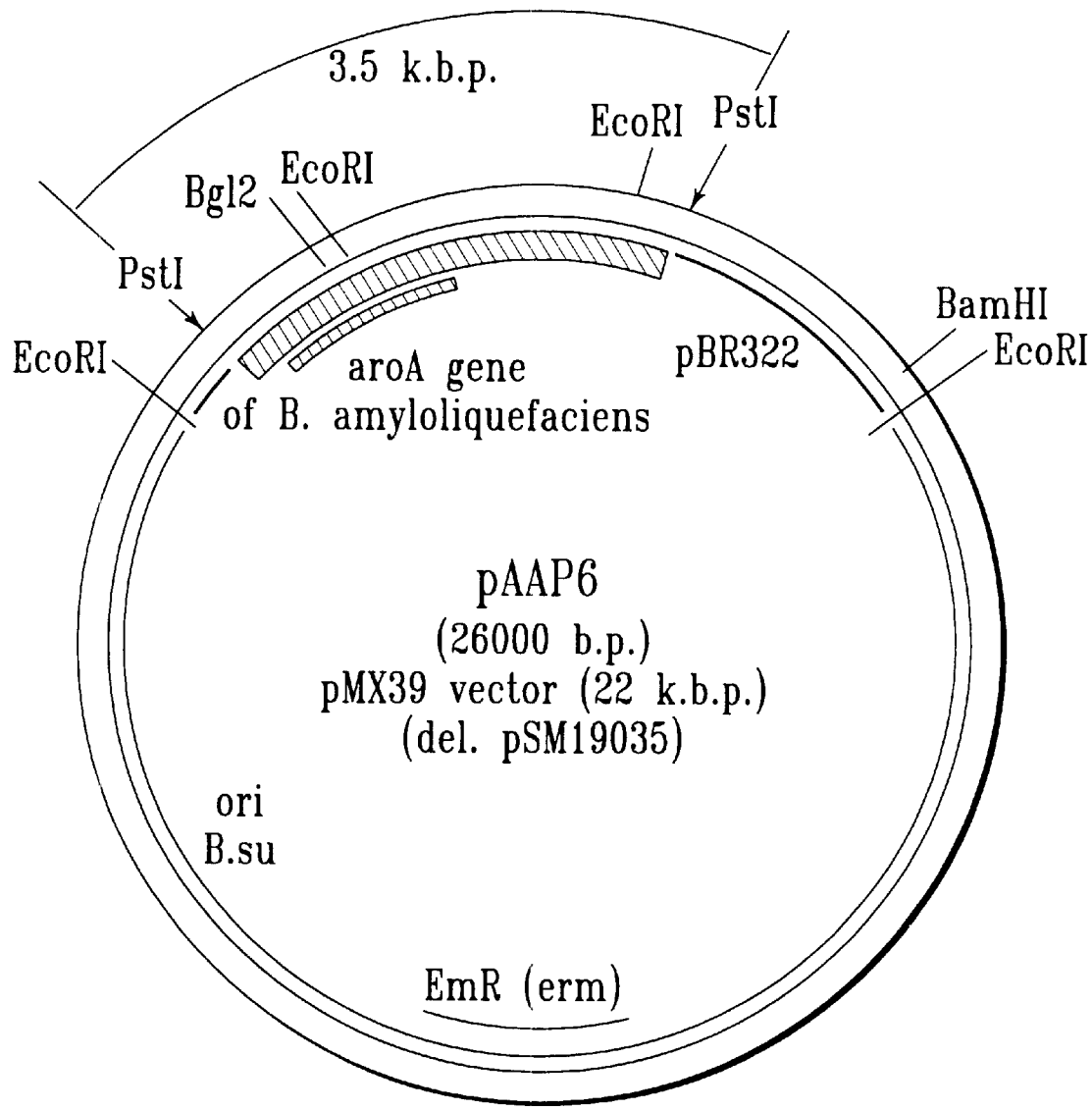

The aroA gene encodes DAHP-synthase, first enzyme of aromatic substances biosynthesis. The 3.5 kb DNA fragment carrying the aroA gene of B. amyloliquefaciens A50 strain was cloned on low copy vector pMX39 (Em$^R$) in B. subtilis WB2281 aroA6 recipient (FIG. 10). The resulted recombinant plasmid pAAP6 (AroA$^+$, Em$^R$) was stable and did not segregated from B. subtilis cells during growth in medium without antibiotic erythromycin.

B. subtilis aroA6 harboring pAAP6 has been deposited in Russian National Collection of Industrial microorganisms (VKPM) Depositary, GNIIgenetika; 1, Dorozhny Proezd., 1,113545, Moscow, Russia, under a Registration number of VKPM B-7698 from Dec. 3, 1998.

The plasmid pAAP6 was transferred into shikimate producer B. subtilis ID3. The resulted strain was named as B. subtilis ID36 (ID3/pAAP6). Its genotype is aroI116, amy4, amy::$Pr_{(rpmA)}$-aroD$^{(+)}$-pheA/pAAP6 (erm, aroA$^{(+)}$). The ID36 is aromatic amino acid auxotroph because of aroI116 mutation, and resistant to erythromycin (10 mg/l).

The B. subtilis ID36 strain produced 18–19 g/l shikimate in laboratory fermenters in not finally optimized conditions (Table 3). It was found that feeding rate by glucose influenced to shikimate production. The feeding rate at 3 g/l.h was best for the present conditions when initial fermentation medium had 100 g/l glucose or lower concentration of glucose. In addition, the lower or higher feeding rate reduced productivity. The absence of glucose in initial fermentation medium increased productivity up to 20 g/L.

TABLE 3

Shikimate production by Bacillus subtilis 1D36 strain in laboratory fermenters (1 L)

| Strain | Additional genes | Time hours | OD 560 nm | Shikimate g/l | Dehydro-Shikimate g/l | Ratio DHSH/SH |
|---|---|---|---|---|---|---|
| ID36 (ID3/ pAAP6) | AroD in Chromosome aroA on Plasmid | 28 | 56 | 4.4 | 6.0 | 1.4 |
| | | 52 | 60 | 13.9 | 9.7 | 0.7 |
| | | 66 | 64 | 16.7 | 10.9 | 0.65 |
| | | 73 | 64 | 18.6 | 10.3 | 0.55 |
| | | 90 | 62 | 19.7 | 9.8 | 0.5 |

DAHP-synthase activity of the strains carrying pAAP6 plasmid was measured. As a result, DAHP-synthase activity of these strains had 5 times higher than that of a strain without plasmid (Table 4).

TABLE 4

DAHP-synthase activity in crude extracts of B. subtilis shikimate producers

| Strains | Additional genes | DAHP-synthase activity (nm/min · mg) |
|---|---|---|
| aroI116 | No | 13 |
| ID3 | aroD in chromosome | 13 |
| ID36 (ID3/pAAP6) | aroD in chromosome aroA on plasmid pAAP6 | 67 |

EXAMPLE 3

Optimization of Expression of the aroD Gene Encoding Shikimate Dehydrogenase

The aroD gene dose and shikimate dehydrogenase activity was increased in B. subtilis ID3 strain by transformation with DNA of pDP4 plasmid (Table 1). By using the temperature shift and antibiotic concentrations several new strains were constructed.

B. subtilis ID34-37-5 was constructed by transformation of ID3 with pDP4 and selection by cultivation at 37C on a medium containing 5 mg/l of Cm.

B. subtilis ID34.50.5 was constructed by transformation of ID3 with pDP4 and selection by cultivation at 50C on a medium containing 5 mg/l of Cm followed by growing at 37C on 5 mg/l of Cm. The aroD genes of B. amyloliquefaciens which were carried in the plasmid pDP4 and the chromosome of B. subtilis ID3 strain have homology. The plasmid can not autonomously replicate in bacteria at non-permissive temperature 50° C. but is able to integrate in chromosome by using homology of aroD genes. Therefore, the clones with integrated plasmid were able to be selected by cultivation at 50° C.

B. subtilis ID34.50.100 was constructed by growing B. subtilis ID34.50.5 at 37C on a medium containing 100 mg/l of Cm. The two integrated aroD copies in chromosome of ID34.50.5 form the structure of direct repeats and cat-gene between them. ID34.50.5 was used to generate the aroD and cat gene amplification by growing bacteria in high concentration of chloramphenicol.

The shikimate dehydrogenase activity in B. subtilis ID3 derivatives which carry pDP4 plasmid was very high. It increased up to 150–200 times than aroI116 (Table 5). However, the pDP4 plasmid is segregationally unstable. This problem will be solved later by using stable vectors and multi-integration of aroD gene in chromosome.

TABLE 5

Shikimate dehydrogenase activity in crude extracts of B. subtilis shikimate producers

| Strains | Additional genes | Shikimate dehydrogenase activity (nm/min · mg) |
|---|---|---|
| aroI116 | No | 5 |
| ID3 | aroD in chromosome | 43 |
| ID36 (ID3/pAAP6) | aroD in chromosome aroA on plasmid pAAP6 | 42 |
| ID34.37.5 (ID3/pDP4) | aroD in chromosome aroD on plasmid pDP4 | 560 |
| ID34.50.5 (ID3/pDP4) | aroD in chromosome aroD on plasmid pDP4 | 710 |
| ID34.50.100 (ID3/pDP4) | aroD in Chromosome aroD on plasmid pDP4 | 1090 |

EXAMPLE 4
Integration of aroA Gene into Chromosome of Bacillus subtilis ID3

Figure 11:
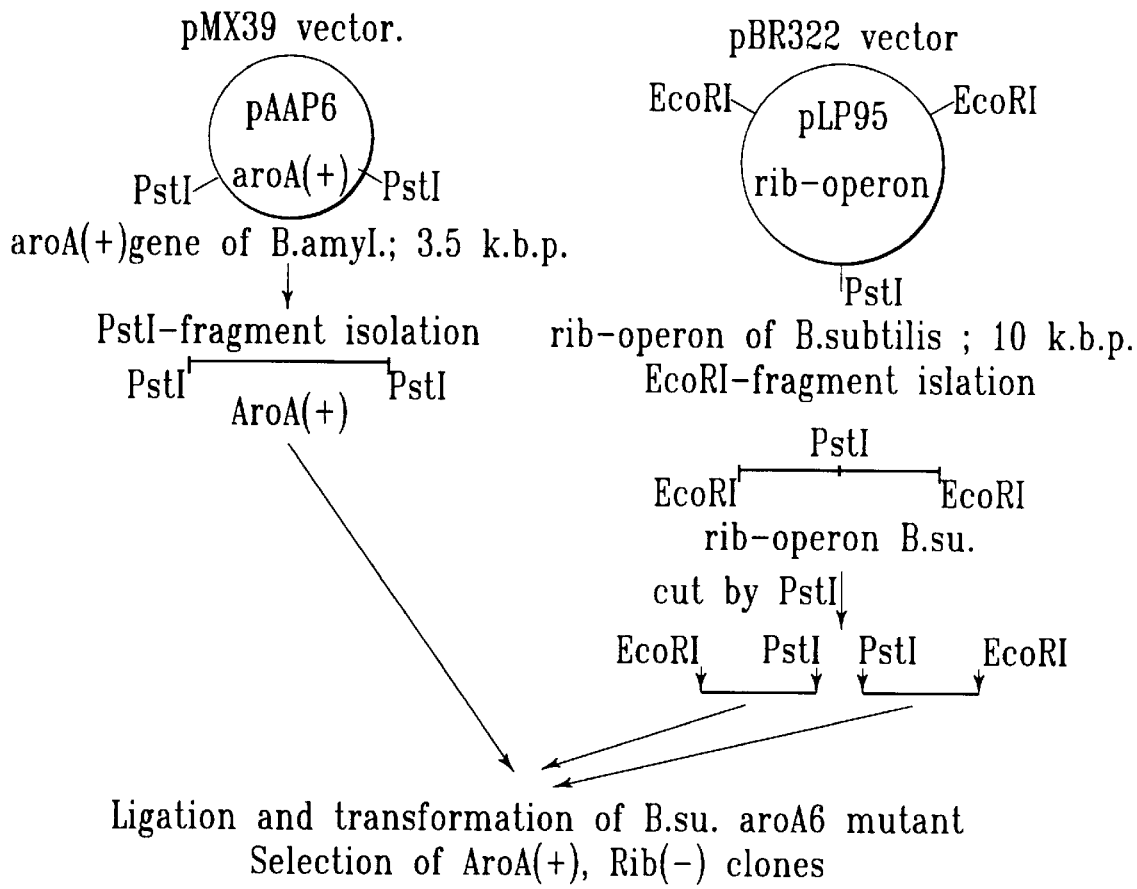
Figure 11:
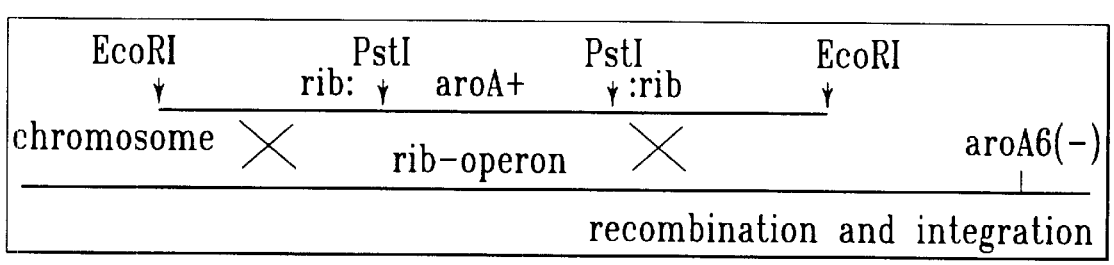

The aroA gene was integrated into riboflavin biosynthesis operon on the chromosome of ID3 strain (FIG. 11). A DNA fragment containing riboflavin biosynthesis operon (rib-operon) was obtained by digesting a plasmid pLP95 which includes rib-operon derived from Bacillus subtilis with EcoRI. The DNA fragment was digested with EcoRI to obtain two EcoRI-PstI fragments. These EcoRI-PstI fragments were ligated with a DNA fragment including aroA gene, which was obtained by digesting pAAP6 (AroA$^+$, Em$^R$) with PstI and transformed into Bacillus subtilis WB2281 aroA6. A resulting transformant, Bacillus subtilis F8 strain, exhibiting phenotype of AroA$^+$ and Em$^R$ has the aroA(+) gene which is integrated into internal region of rib-operon on the chromosome.

Then, the chromosomal DNA was isolated and mixed with helper plasmid pMX39 (Em$^R$). Using the mixture Bacillus subtilis was transformed and an Em$^R$ clone was selected. The resulted strain ID4 (ribG::aroA(+)) has 3-times higher DAHP synthase activity (Table 6). Production of shikimic acid and dehydroshikimic acid by Bacillus subtilis ID3 and ID4 in laboratory fermenters (1L) is shown in Table 7.

TABLE 6

| Strains | Integrated genes of B. amyloliquefaciens | DAHP-synthase activity (nm/min · mg) |
|---|---|---|
| ID3 | AroD in chromosome | 7 |
| ID4 | AroD in chromosome, AroA in chromosome | 24 |

TABLE 7

| Strains | Integrated genes into chromosome of B. amyloliquefaciens | Time | OD$_{560}$ | Shikimate | Dehydro-shikimate (g/L) |
|---|---|---|---|---|---|
| ID3 | AroD(+) gene in chromosome; Amy(−); Aro(−) | 23 | 43 | 4.8 | 0.8 |
|  |  | 43 | 53 | 12.1 | 2.6 |
|  |  | 51 | 53 | 14.8 | 3.7 |
|  |  | 66 | 54 | 16.5 | 4.4 |
|  |  | 90 | 47 | 17.3 | 4.5 |
| ID4 | AroD(+) and aroA(+) gene in chromosome; Amy(−); Aro(−); Rib(−) | 23 | 43 | 4.1 | 0.9 |
|  |  | 43 | 45 | 9.6 | 2.5 |
|  |  | 51 | 38 | 10.6 | 2.2 |
|  |  | 66 | 30 | 10.6 | 1.8 |
|  |  | 90 | 29 | 11.3 | 2.1 |

EXAMPLE 5
Construction of Riboflavin Prototrophic Strain Derived From ID4

To complement riboflavin auxotrophy in ID4 strain ribG gene of B. amyloliquefaciens was integrated into chromosome of ID4. Thus resulting strain ID5 [ribG::aroA(+), xyz::ribG(B.am)] was constructed. Production of shikimic acid and dehydroshikimic acid by the strains ID3, ID4 and ID5 in tubes in minimal OSM100 medium are is shown in Table 8.

TABLE 8

| Strain | ID3 | ID4 | ID5 |
|---|---|---|---|
| Targets in chromosome and integrated genes of B. amyloliquefaciens | Amy::aroD(+) | amy::aroD(+) rib::aroA(+) | amy::aroD(+) rib::aroA(+) xyz::ribG(+) |
| Shikimic acid (g/L) | 6.3 | 5.7 | 5.1 |
| Dehydroshikimic acid (g/L) | 0.8 | 0.9 | 0.6 |

(Minimal medium "OSM100" for fermentation in tubes)

| | |
|---|---|
| K$_2$HPO$_4$.3H$_2$O | 1.83% |
| KH$_2$PO$_4$ | 0.6% |
| Urea | 0.6% |
| maltose | 4% |
| sucrose | 8% |
| MgSO$_4$.7H$_2$O | 0.1% |
| FeSO$_4$ | 0.001% |
| MnSO$_4$ | 0.001% |
| L-trp | 0.01% |
| L-tyr | 0.01% |
| L-phe | 0.01% |

EXAMPLE 6
Construction of Shikimic Acid Producer Which is Deficient in aroE Gene Encoding 5-enolpyruvylshikimate-3-phosphate Synthase and Having Shikimate Kinase The laboratory strain B. subtilis SB130 (aroE130 hisH32) was analyzed for shikimic acid productivity. B. subtilis SB130 (aroE130 hisH32) has been deposited in Russian National Collection of Industrial Microorganisms (VKPM) Depositary, GNIIgenetika; 1, Dorozhny Proezd., 1,113545, Moscow, Russia, under a Registration number of VKPM B-1730, and also deposited in Bacillus Genetic Stock Center, The Ohio State University, Department of Biochemistry, 484 West Twelfth Avenue, Columbus, Ohio 43210 USA, under a Registration number of BGSC 1A133. The SB130 strain was fermented in OSM100 medium in tubes at 37° C. in 90 hours. The HPLC analysis showed that strain accumulated 1.1 g/L of shikimic acid and 0.16 g/L of dehydroshikimic acid (Table 9). Theoretically this strain is able to accumulate shikimate 3-phospate, but accumulation of shikimic acid was found. It is possible that phosphatases of B. subtilis cut off phosphate group from shikimate 3-phospate and converted into shikimic acid.

Thus the inventors found that shikimic acid is produced not only by aroI116 but also by aroE130 mutants of B. subtilis. Then the new shikimate producer strain was constructed, which carries the aroE130 mutation in the gene encoding the 5-enolpyruvylshikimate-3-phosphate synthase and do not carries aroI116 mutation in the shikimate kinase gene. Such strain was constructed from ID3 strain in three steps:

(1) The B. subtilis ID3 strain carrying aroI116 (Aro$^-$) mutation was transformed with 1050bp of linear HindIII DNA fragment containing the cloned aroI gene of B. subtilis 168 to obtain the prototrophy (Aro$^+$). The aroI gene of B. subtilis had been cloned and sequenced (datebase "SWISS-PROT:P37944"; Nakane A. et al., J. Ferment. Bioeng., 77 (2), 312–314, (1994). In this experiment the DNA of plasmid pGI502, constructed on basis of E. coli vector pTZ19RJL1 was used. Aro$^+$ transformants on minimal medium was selected and named as B. subtilis D4. Its genotype is amy4, amy::Pr$_{(rpmA)}$-aroD$^{(+)}$-pheA and phenotype is Aro$^+$ and Amy$^-$. The strain D4 did not produced shikimic acid.

(2) The aroE130 mutation was transferred into B. subtilis D4 strain by using gene conversion method (Iglesias A. and Trautner T. A., Mol. Gen. Genet., 189:73–76 (1983)) with a plasmid carrying cloned aroE gene and containing aroE130 mutation in it.

The B. subtilis aroE(+) gene had been cloned on pTP72 plasmid. To clone the aroE(+) gene the B. subtilis chromosomal DNA was cut by EcoRI restriction enzyme and ligated with pCB20 plasmid (mentioned earlier) DNA EcoRI-fragments. The DNA was transformed into B. subtilis trpE1733 recE4 recipient strain and Em$^R$, Trp$^+$ clones were selected. The isolated recombinant plasmid was named as pTP72. The pTP72 plasmid transformed to prototrophy B. subtilis strains containing following mutations :trpE1733, trpE8, trpD10, trpC2, trpF5, trpB3, trpA1722, trpA4, hisH32, tyrA and aroE130. The pTP72 plasmid (26.4 kbp) carry the all tryptophane operon genes, hisH, tryA and aroE genes of B. subtilis cloned on pCB20 (Em$^R$) vector on single 19 kbp EcoRI fragment. B. subtilis SB130 aroE130 hisH32 was transformed by the plasmid pTP72. The Em$^R$ transformants were selected and tested for the presence of Aro$^-$ phenotype. The aroE130 mutation was transferred from chromosome into plasmid by "gene conversion". The two different alleles aroE130//aroE$^+$ of the same gene were converted into one aroE130 with 4% of frequency. The plasmid in which aroE$^+$ gene was converted to aroE130 was named as pTP72aroE130.

(3) B. subtilis strain D4 was transformed by the plasmid pTP72aroE130. The Aro$^-$ clones were selected among Em$^R$ transformants. The aroE130 mutation was transferred from pTP72aroE130 plasmid into chromosome of B. subtilis D4 by "gene conversion" with 4% of frequency. The resulted strain B. subtilis D4 aroE130/pTP72 aroE130 carried aroE130 mutation in the chromosome and on the plasmid in aroE gene. The plasmid was eliminated from strain at 50° C. The resulted strain was named as B. subtilis strain DE1. Its genotype is aroE130, amy4, amy::Pr$_{(rpmA)}$-aroD$^{(+)}$-pheA and phenotype is Aro$^-$, Amy$^-$. The strain DE1 strain has the minus mutation in aroE gene encoding the 5-enolpyruvylshikimate-3-phosphate synthase.

The B. subtilis strain DE1 (aroE130) produced 2.8 g/L of shikimic acid and 0.18 g/L of dehydroshikimic acid in tubes in OSM100 medium at 37° C. in 90 hours (Table 9).

TABLE 9

| Strain | D4 | SB130 | DE1 | ID3 |
|---|---|---|---|---|
| Auxotrophic Mutations | Prototroph | aroE130 hisH32 | aroE130 | AroI116 |
| Targets in chromosome and integrated genes of B. amyloliquefaciens | amy::aroD$^+$ | — | amy::aroD$^+$ | amy::aroD$^+$ |
| Shikimic acid (g/L) | 0 | 1.1 | 2.8 | 6 |
| Dehydroshikimic acid (g/L) | 0 | 0.16 | 1.08 | 0.8 |

What is claimed is:

1. A method for producing shikimic acid comprising cultivating in a growth medium a bacterium which produces shikimic acid, allowing shikimic acid to accumulate in the growth medium, and recovering shikimic acid from the growth medium, wherein the bacterium belongs to the genus Bacillus, and wherein the bacterium is modified so that it contains less shikimate kinase activity than in its unmodified form.

2. The method of claim 1, wherein said bacterium is Bacillus subtilis.

3. The method of claim 1, wherein said bacterium is modified so that shikimate dehydrogenase activity of said bacterium is increased in relation to a corresponding wild-type bacterium.

4. The method of claim 3, wherein shikimate dehydrogenase activity is increased by increasing the copy number of a gene encoding shikimate dehydrogenase, modifying the expression regulation sequence of said gene so that the expression of said gene is enhanced, or integrating said gene into chromosomal DNA of said bacterium.

5. The method of claim 1, wherein said bacterium is Bacillus subtilis.

6. The method of claim 4, wherein the shikimate dehydrogenase gene is operably linked to a heterologous promoter, and is integrated into the chromosome of the Bacillus.

7. The method of claim 6 wherein said bacterium is further modified so that activity of 3-deoxy-D-arabino-heptulosonic acid 7-phosphate synthase of said bacterium is increased in relation to that obtained in absence of said further modification.

8. The method of claim 7 wherein said 3-deoxy-D-arabino-heptulosonic acid 7-phosphate synthase activity is increased by increasing the copy number of 3-deoxy-D-arabino-heptulosonic acid 7-phosphate synthase genes in said bacterium, or by modifying an expression regulation sequence of a 3-deoxy-D-arabino-heptulosonic acid 7-phosphate synthase gene so that expression of said gene is increased relative to that obtained in the absence of modification of an expression regulation sequence of a 3-deoxy-D-arabino-heptulosonic acid 7-phosphate synthase gene.

9. The method of claim 8 wherein said shikimate dehydrogenase gene is integrated into the chromosome of said bacterium.

10. A bacterium belonging to the genus Bacillus which produces shikimic acid, wherein said bacterium is modified so that its shikimate kinase activity is less than in the absence of the modification, and wherein said bacterium comprises a second modification which causes it to contain more shikimate dehydrogenase activity than it would in the absence of said second modification.

11. The bacterium of claim 10, wherein said bacterium comprises a third modification which causes it to contain more 3-deoxy-D-arabino-heptulosonic acid 7-phosphate synthase activity than in the absence of said third modification.

12. A method for producing shikimic acid comprising cultivating in a growth medium a bacterium which produces shikimic acid, allowing shikimic acid to accumulate in the growth medium, and recovering shikimic acid from the growth medium, wherein the bacterium belongs to the genus Bacillus, and wherein the bacterium is modified so that it contains less 5-enolpyruvylshikimate-3-phosphate synthase activity than it would in its unmodified form.

13. The method of claim 12, wherein said bacterium is further modified so that it contains more shikimate dehydrogenase activity than it would in its unmodified form.

14. The method of claim 12 wherein said shikimate dehydrogenase activity is increased by increasing the number of shikimate dehydrogenase genes in said bacterium, or by modifying an expression regulation sequence of a shikimate dehydrogenase gene so that expression of said gene is increased.

15. A bacterium belonging to the genus Bacillus which produces shikimic acid, wherein said bacterium is modified so that it contains less 5-enolpyruvylshikimate-3-phosphate synthase activity than it would in its unmodified form, and wherein said bacterium comprises a second modification which causes it to contain more shikimate dehydrogenase activity than it would in the absence of said second modification.

* * * * *